United States Patent [19]

Spicer et al.

[11] 4,130,651
[45] Dec. 19, 1978

[54] BUTAMISOLE INJECTABLE FORMULATIONS HAVING IMPROVED MARGIN OF SAFETY IN DOGS

[75] Inventors: Larry D. Spicer, Princeton; Karl L. Simkins, Jr., Princeton Junction, both of N.J.

[73] Assignee: American Cyanamid Company, Stamford, Conn.

[21] Appl. No.: 892,001

[22] Filed: Mar. 31, 1978

[51] Int. Cl.² .......................................... A61K 31/425
[52] U.S. Cl. .................................................... 424/270
[58] Field of Search ......................................... 424/270

[56] References Cited

U.S. PATENT DOCUMENTS 3,899,583   8/1975   Spicer et al. .......................... 424/270

Primary Examiner—Sam Rosen
Attorney, Agent, or Firm—H. G. Jackson

[57] ABSTRACT

The invention relates to liquid anthelmintic compositions for injection comprising a solution of butamisole salts in aqueous propylene glycol, having an improved margin of safety in dogs, as compared to conventional aqueous buffered solutions of butamisole salts. The present invention also relates to a method for the control of helminths, especially whipworms, in dogs, comprising administering to the animals subcutaneously or intramuscularly an anthelmintically effective amount of a solution of butamisole salts in aqueous propylene glycol.

17 Claims, No Drawings

BUTAMISOLE INJECTABLE FORMULATIONS HAVING IMPROVED MARGIN OF SAFETY IN DOGS

The compound of formula (I):

3'-(2,3,5,6-tetrahydroimidazo[2,1-b]thiazol-6-yl) isobutyranilide, hereinafter also referred to as butamisole, racemic mixtures thereof, optically active isomers thereof as the pharmaceutically acceptable acid addition salts thereof; is highly effective for the control of helminths, especially whipworms, infecting dogs. Among the optically active isomers of butamisole, the l isomer is generally preferred since it appears to be biologically more active than is the corresponding d isomer. The above anthelmintic may be administered to dogs in, or with their feed or drinking water; or may be administered orally in the form of pills, tablets, and the like. This anthelmintic may also be formulated as injectables for subcutaneous or intramuscular administration.

Of the above formulations, injectables are one of the preferred modes of administration since they allow the introduction and delivery of butamisole into the circulatory system of the animal via subcutaneous or intramuscular injections in precisely calculated dosages.

Unfortunately, the water-soluble, pharmaceutically acceptable acid addition salts of butamisole are quite toxic to dogs, and the margin of safety between the maximum effective and minimum toxic dose in these animals is quite small. Thus, an accidentally administered overdose could poison, and might even kill the animal it was supposed to protect. Thus, injectable formulations of butamisole possessing a wider margin of safety in dogs are highly desirable.

Water soluble, pharmaceutically acceptable acid addition salts of the above anthelmintic administered as conventional aqueous solutions to dogs, subcutaneously or intramuscularly, are rapidly absorbed from the site of the injection, and will reach the circulatory system of the animal in a relatively short period of time. Thus anthelmintically effective amounts of butamisole will appear in the dogs circulatory system when this compound is administered subcutaneously or intramuscularly at or below the recommended maximum dosage of 2.5 mg/kg body weight for these animals. The level thus obtained is maintained only for a short period of time, after which the active compound is rapidly eliminated from the animals circulatory system.

As stated above, it would be advantageous and highly desirable to find injectable formulations of butamisole with a wider margin of safety, which would protect dogs from an accidental overdosage. Such a formulation would also allow, if so desired, the administration of higher than the recommended dosages, without causing more than transient symptoms of adverse drug reaction in the animals. Dogs receiving higher than normal dosages of the above anthelmintic by accident or by design could then be expected to recover rapidly and without lasting damage.

We now find, that injectable formulations comprising a solution of a compound of formula (I):

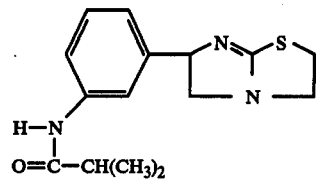

racemic mixtures thereof, optically active isomers thereof as the pharmaceutically acceptable acid addition salts thereof, in aqueous propylene glycol are inherently safer compared to conventional aqueous buffered solutions of same. We also find, that overdosages of three times the recommended maximum dosage are well tolerated by most recipient animals with only transient toxic symptoms accompanying such overdosages, while a similar overdosage given in the form of conventional aqueous buffered injectables usually kill the recipient animal in a relatively short time.

Conveniently, the liquid anthelmintic compositions of the present invention may be prepared as follows:

1% to 4% weight by volume, and preferably 1.1% to 2.5% weight by volume of a compound of formula (I):

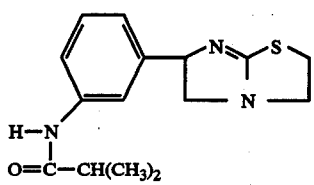

racemic mixtures thereof, optically active isomers thereof, and pharmaceutically acceptable acid addition salts thereof, wherein the acids are preferably hydrochloric acid, sulfuric acid and phosphoric acid; 60% to 80% weight by volume, and preferably 70% weight by volume of propylene glycol; 1% to 5% weight by volume, and preferably 4% weight by volume of benzyl alcohol are mixed, and water is added to adjust the volume of the mixture to 100%. The mixture is then agitated, if necessary, until a clear solution forms.

A preferred formulation comprises 1.1% weight by volume butamisole hydrochloride, 70% by weight by volume of propylene glycol, 4% weight by volume of benzyl alcohol and water to adjust the volume of the formulation to 100%.

For the control of helminths, especially whipworms, infecting dogs, the above formulations are administered to the animals as one or more subcutaneous or intramuscular injection(s), in dosages designed to deliver 2.5 mg butamisole equivalent /kg body weight.

The following, non-limiting examples are provided to further illustrate the invention.

EXAMPLE 1

Preparation of injectable formulations of Butamisole.

| Composition of Injectables | | |
|---|---|---|
| | Percent w/v | |
| Ingredients | A | B |
| Butamisole . HCl (95.44%) | 1.1 | 1.1 |
| Propylene glycol | 70.0 | — |
| Benzyl alcohol | 4.0 | — |
| Methyl Paraben | — | 0.16 |
| Propyl Paraben | — | 0.016 |
| Sodium hydroxide | — | 0.047 |
| Sodium metabisulfite | — | 0.10 |
| Disodium Edetate | — | 0.10 |
| Citric Acid. 2H$_2$O | — | 3.47 |
| Sodium Citrate. 2H$_2$O | — | 2.08 |
| Distilled water q.s. ad | 100 ml | 100 ml |
| Specific gravity | 1.039 | 1.024 |

*= In grams, except for water.

The above ingredients are mixed, part of the water added, and the mixture is stirred until a clear solution forms. The volume of the solutions is then adjusted to 100 ml with distilled water, and the solutions are filtered aseptically.

EXAMPLE 2

Evaluation of the margin of safety of the novel injectables of the invention in dogs.

Animals

Fifteen adult mongrel dogs (nine males and six females) weighing 7.8 to 21.3 kg, and nine adult Beagles (three males and six females) weighing 9.0 to 14.4 kg prior to treatment are used in the experiment.

Procedure

At 8 days prior to drug administration the 24 dogs are allotted to three groups of eight animals each on the basis of breed and body weight so that the average weights per group are approximately equal. Assignment of groups to treatments is by random selection. All dogs are housed in individual cages.

Each dog is provided daily with 350 g of a commercial Dog Chow (composition of same is reported below) in the morning throughout the experiment except for the day of drug administration. On that day the dogs are not fed in the morning but the ration is provided at 4:00 p.m. after the clinical symptoms subside. Water is provided ad libitum throughout the experiment. All dogs are weighed on the day prior to treatment for calculation of drug dosages.

Dogs in Group I serve as controls and are subcutaneously injected with 5 ml normal saline per animal. Animals in Groups II and III receive 7.5 mg butamisole .HCl/kg body weight subcutaneously as a 1.1% w/v solution in 70% propylene glycol or as a 1.1% w/v aqueous solution, respectively. All animals are observed after treatment continuously for 6 hours, and periodically during the experimental period for toxicological symptoms.

Clinical symptoms and survival ratios are summarized in Table I below.

| Composition of Commercial Dog Chow. | |
|---|---|
| Nutrient | Minimum Quantities in Dog Chow |
| Protein | 26.0% |
| Fat | 10.0% |
| Linoleic acid | 1.3% |
| Calcium | 1.6% |
| Phosphorus | 0.95% |
| Potassium | 0.65% |
| Sodium Chloride | 1.1% |
| Magnesium | 0.15% |
| Iron | 200 mg/kg |
| Copper | 13 mg/kg |
| Manganese | 56 mg/kg |
| Zinc | 80 mg/kg |
| Iodine | 2.2 mg/kg |
| Selenium | 0.1 mg/kg |
| Vitamin A | 17,600 IU/kg |
| Vitamin D | 1,760 IU/kg |
| Vitamin E | 45 IU/kg |
| Thiamine (Vitamin B$_1$) | 7.3 mg/kg |
| Riboflavin (Vitamin B$_2$) | 4.5 mg/kg |
| Pantothenic Acid | 9.0 mg/kg |
| Niacin | 47.0 mg/kg |
| Pyridoxine (Vitamin B$_6$) | 7.0 mg/kg |
| Folic Acid | 1.3 mg/kg |
| Biotin | 0.13 mg/kg |
| Vitamin B$_{12}$ | 0.025 mg/kg |
| Choline | 1,100 mg/kg |

TABLE I

Evaluation of the margin of safety of the injectables of the present invention in dogs, Compared to normal aqueous buffered injectables containing the same drug.

| Group | Treatment | Clinical Observations | No. of Dogs showing at least one of the symptoms | Onset hours | Duration hours | Survivors per total |
|---|---|---|---|---|---|---|
| I | Controls. 5 ml normal saline/dog | Normal | 0 | 0 | 0 | 8/8 |
| II | Example 1 Sample A* | Tremors, Ataxia; foamy muzzle; hyperexcitement; emesis and death. | 2 | 2 | 3 | 7/8 |
| III | Example 1 Sample B* | Tremors, Ataxia; salivation; slight relaxation of nictitating membrane; lateral recumbency and death. | 8 | 0.5 | 2 | 0/8 |

*Injected subcutaneously at a rate providing 7.5 mg butamisole HCl/kg body weight.

EXAMPLE 3

Evaluation of the Margin of Safety of a 2.5% w/v Butamisole.HCl/Propylene Glycol Injectable Solution in Dogs.

Injectable Solution.

By the procedure of Example 1, an injectable solution is prepared, having the following composition:

| Ingredients* | % w/v |
|---|---|
| Butamisole. HCl | 2.5 |
| Propylene glycol | 70.0 |
| Benzyl alcohol | 5.0 |
| Distilled water, q.s. ad. | 100.0 ml |

*In grams, except for water.

Animals.

Eighteen adult beagles and six puppies are randomly distributed into three groups of six adults (three males and three females) and two puppies. All the animals are placed in individual cages.

Procedure.

The animals in Group I serve as controls, and receive 70% propylene glycol (aqueous) at the rate of 1 ml/4.5 kg body weight, injected subcutaneously. Animals in Groups II and III receive the above preparation subcutaneously at the rate of 2.5 and 7.5 mg/kg body weight, respectively.

The animals are observed after treatment continuously for 4 hours and periodically the rest of the experimental period for toxicological symptoms.

Findings.

No symptoms of toxicity are observed after the dosing of the drug at either of the two rates of administration.

The animals continued to gain weight post-treatment

Six days post-treatment, the animals are necropsied and examined for gross pathology. No significant deviations from norms are found, indicating the safety of the above 2.5% w/v solution of Butamisole.HCl in 70% propylene glycol when administered at 2.5 and 7.5 mg/kg body weight, respectively.

We claim:

1. A liquid anthelmintic composition for injection comprising an anthelmintically effective amount of a solution of a compound of formula:

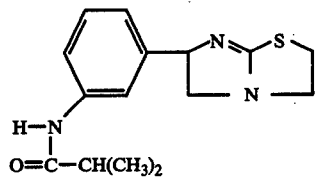

the racemic mixtures, the optical isomers thereof as the pharmaceutically acceptable acid addition salts thereof in aqueous propylene glycol.

2. A liquid composition according to claim 1, wherein the compound is the racemic mixture.

3. A liquid composition according to claim 1, wherein the compound is the l isomer.

4. A liquid composition according to claim 1, wherein the pharmaceutically acceptable acids are hydrochloric acid, sulfuric acid or phosphoric acid.

5. A liquid composition according to claim 1, wherein the solution contains the compound in an amount corresponding to 1% to 4% weight by volume, propylene glycol in an amount corresponding to 60% to 80% weight by volume, benzyl alcohol in an amount corresponding to 1% to 5% weight by volume; and water in an amount sufficient to adjust the volume of the composition to 100%.

6. A liquid composition according to claim 1, wherein the solution contains the compound in an amount corresponding to 1.1% weight by volume, propylene glycol in an amount corresponding to 70% weight by volume, benzyl alcohol in an amount corresponding to 4% weight by volume, and water in an amount sufficient to adjust the volume of the composition to 100%.

7. A liquid composition according to claim 6, wherein the solution contains the hydrochloride of the racemic compound in an amount corresponding to 1.1% weight by volume.

8. A liquid composition according to claim 6, wherein the solution contains the hydrochloride of the l isomer of the compound in an amount corresponding to 1.1% weight by volume.

9. A method for the control of helminths infecting dogs, comprising administering parenterally to the animals an anthelmintically effective amount of a liquid anthelmintic composition for injection comprising a solution of a compound of formula:

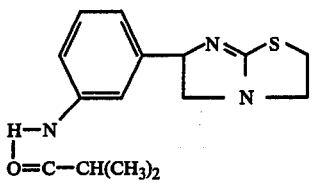

the racemic mixtures, the optical isomers thereof as the pharmaceutically acceptable acid addition salts thereof in aqueous propylene glycol.

10. A method according to claim 9, wherein the compound is the racemic mixture.

11. A method according to claim 9, wherein the compound is the l isomer.

12. A method according to claim 9, wherein the pharmaceutically acceptable acids are selected from hydrochloric acid, sulfuric acid or phosphoric acid.

13. A method according to claim 9, wherein the liquid composition contains the compound in an amount corresponding to 1% to 4% weight by volume; propylene glycol in an amount corresponding to 60% to 80% weight by volume; benzyl alcohol in an amount corresponding to 1% to 5% weight by volume, and water in an amount sufficient to adjust the volume of the composition to 100%.

14. A method according to claim 9, wherein the liquid composition contains the compound in an amount corresponding to 1.1% weight by volume; propylene glycol in an amount corresponding to 70% weight by volume; benzyl alcohol in an amount corresponding to 4% weight by volume, and water in an amount sufficient to adjust the volume of the composition to 100%.

15. A method according to claim 9, wherein the liquid composition contains the hydrochloride of the racemic compound in an amount corresponding to 1.1% weight by volume.

16. A method according to claim 9, wherein the liquid composition contains the hydrochloride of the l isomer of the compound in an amount corresponding to 1.1% weight by volume.

17. A method according to claim 9, wherein the helminths are whipworms.

* * * * *